(12) United States Patent
Hagihara et al.

(10) Patent No.: US 8,227,480 B2
(45) Date of Patent: Jul. 24, 2012

(54) INDAZOLE DERIVATIVE HAVING SPIRO RING STRUCTURE IN SIDE CHAIN

(75) Inventors: Masahiko Hagihara, Ube (JP); Yasunori Tsuzaki, Ube (JP); Ken-ichi Komori, Ube (JP); Hiroshi Nishida, Ube (JP); Kazutaka Kido, Ikoma (JP); Tomokazu Fujimoto, Ikoma (JP); Takeshi Matsugi, Ikoma (JP); Atsushi Shimazaki, Ikoma (JP)

(73) Assignees: Ube Industries, Ltd., Yamaguchi (JP); Santen Pharmaceutical Co., Ltd., Osaka (JP)

( * ) Notice: Subject to any disclaimer, the term of this patent is extended or adjusted under 35 U.S.C. 154(b) by 681 days.

(21) Appl. No.: 12/227,890

(22) PCT Filed: Jun. 8, 2007

(86) PCT No.: PCT/JP2007/061598
§ 371 (c)(1),
(2), (4) Date: Dec. 1, 2008

(87) PCT Pub. No.: WO2007/142323
PCT Pub. Date: Dec. 13, 2007

(65) Prior Publication Data
US 2009/0170887 A1    Jul. 2, 2009

(30) Foreign Application Priority Data
Jun. 8, 2006   (JP) .................... 2006-159501

(51) Int. Cl.
| *A01N 43/42* | (2006.01) |
|---|---|
| *A61K 31/44* | (2006.01) |
| *C07D 211/00* | (2006.01) |
| *C07D 213/00* | (2006.01) |
| *C07D 215/00* | (2006.01) |
| *C07D 217/00* | (2006.01) |
| *C07D 219/00* | (2006.01) |
| *C07D 221/00* | (2006.01) |

(52) U.S. Cl. ........................ 514/278; 546/15

(58) Field of Classification Search .................. 514/278; 546/15
See application file for complete search history.

(56) References Cited

U.S. PATENT DOCUMENTS
| 2004/0138286 A1 | 7/2004 | Imazaki et al. |
| 2007/0129404 A1 | 6/2007 | Hagihara et al. |

FOREIGN PATENT DOCUMENTS
| WO | WO 97/23222 A1 | 7/1997 |
| WO | WO 98/06433 A1 | 2/1998 |
| WO | WO 99/64011 A1 | 12/1999 |
| WO | WO 00/09162 A1 | 2/2000 |
| WO | WO 00/57914 A1 | 10/2000 |
| WO | WO 01/56988 A1 | 8/2001 |
| WO | WO 02/076976 A2 | 10/2002 |
| WO | WO 02/076977 A2 | 10/2002 |
| WO | WO 2005/080394 A1 | 9/2005 |
| WO | WO 2005/082890 A1 | 9/2005 |

OTHER PUBLICATIONS

J. G. Cannon (Chapter Nineteen in Burger's Medicinal Chemistry and Drug Discovery, Fifth Edition, vol. I: Principles and Practice, Wiley-Interscience 1995, pp. 783-802, 784).*

* cited by examiner

*Primary Examiner* — Marcos Sznaidman
(74) *Attorney, Agent, or Firm* — Holtz, Holtz, Goodman & Chick, P.C.

(57) ABSTRACT

An object of the present invention is to create a novel indazole derivative having a spiro ring structure in a side chain, which is useful as a pharmaceutical, and to find a new pharmacological activity of the derivative. The present invention compound is represented by the general formula [I] and has an excellent Rho kinase inhibitory activity. In the formula, the ring X represents a benzene ring or a pyridine ring; $R^1$ and $R^2$ represent halogen, H, OH, alkoxy, cycloalkyloxy, aryloxy, alkyl, cycloalkyl or the like; $R^3$ represents halogen, H or the like; $R^4$ and $R^5$ represent halogen, H or the like; $R^6$ and $R^7$ represent H, alkyl or the like; and m, n, p and q represent an integer of 0 to 3. In this connection, each group may have a substituent.

9 Claims, 1 Drawing Sheet

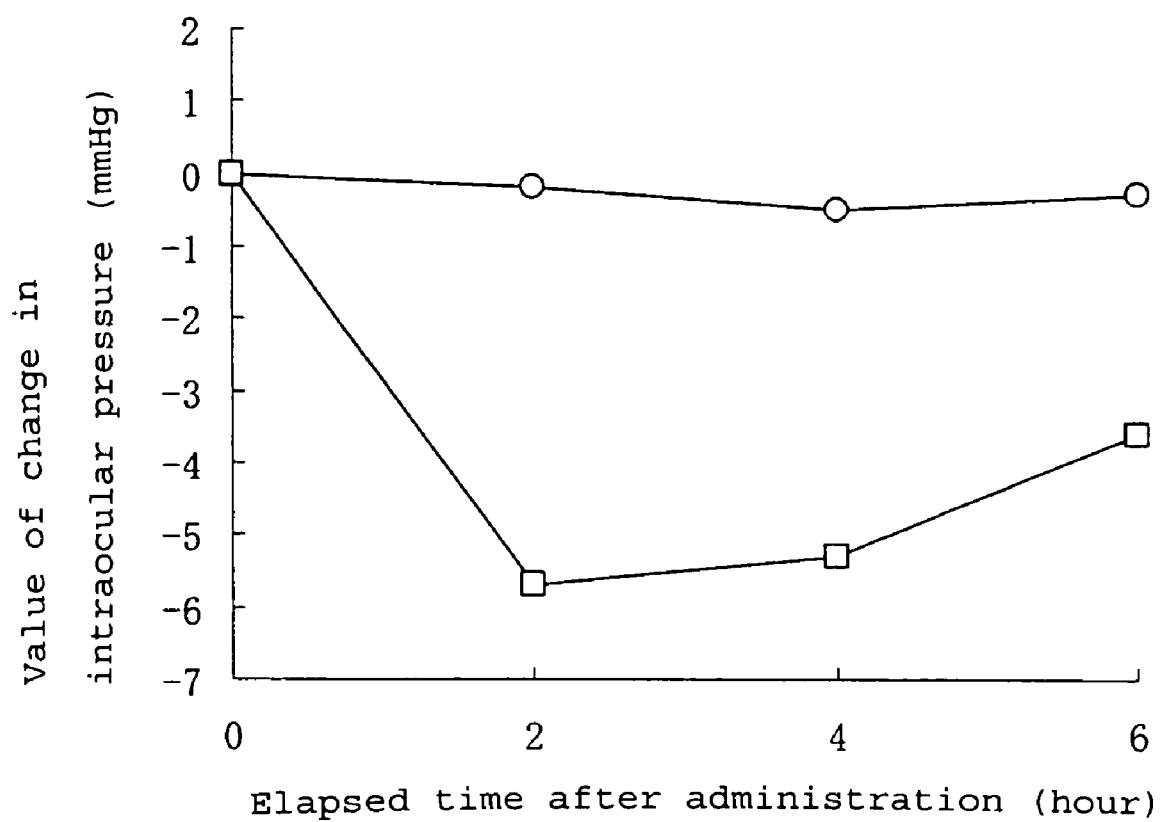

INDAZOLE DERIVATIVE HAVING SPIRO RING STRUCTURE IN SIDE CHAIN

This application is the United States national phase application of International Application PCT/JP2007/061598 filed Jun. 8, 2007.

TECHNICAL FIELD

The present invention relates to a novel indazole derivative having a spiro ring structure in a side chain or a salt thereof, which is useful as a pharmaceutical. The indazole derivative according to the present invention has a Rho kinase inhibitory activity and is useful as a therapeutic agent for diseases associated with Rho kinase such as eye diseases including glaucoma.

BACKGROUND ART

Rho, a low molecular weight GTP-binding protein, is activated by signals from various cell membrane receptors. The activated Rho functions, via Rho kinase signal transduction pathway and actomyosin signal transduction pathway, as a molecular switch for various cellular phenomena such as contraction of smooth muscles, morphological changes in cells, cell movement, cell division, intercellular adhesion, platelet aggregation, leukocyte aggregation, and infiltration and increase of cancer cells.

It has also been known that such cellular phenomena deeply participate in diseases such as hypertension, angina pectoris, asthma, peripheral circular disorder, premature delivery, arteriosclerosis, cancer, inflammatory diseases, autoimmune diseases, AIDS, fertilization and implantation of a fertilized egg, osteoporosis, brain dysfunction, gastrointestinal dysfunction by bacteria, glaucoma and retinopathy.

Accordingly, it is believed that, when Rho is inhibited, prevention and/or treatment of the above-mentioned diseases associated with Rho are/is possible.

On the other hand, it has also been known that, when Rho kinase, which is present in the downstream of signal transduction pathway mediated by Rho, is inhibited, various cellular phenomena caused by Rho can be suppressed.

That is, compounds which inhibit the Rho kinase are believed to be effective preventive and/or therapeutic agent(s) for the above-mentioned diseases associated with Rho such as hypertension, angina pectoris, asthma, peripheral circular disorder, premature delivery, arteriosclerosis, cancer, inflammatory diseases, autoimmune diseases, AIDS, fertilization and implantation of a fertilized egg, osteoporosis, brain dysfunction, gastrointestinal dysfunction by bacteria, glaucoma and retinopathy (WO 98/06433).

A Rho kinase inhibitor is generally defined as an inhibitor of serine/threonine kinase activated as a result of activation of Rho. The Rho kinase inhibitor includes compounds which inhibit ROKA (ROCK-II) or ROKβ (ROCK-I, p160ROCK) and other compounds which inhibit proteins having a serine/threonine kinase activity.

Examples of the known Rho kinase inhibitor include amide derivatives disclosed in WO 98/06433; isoquinoline sulfonyl derivatives disclosed in WO 97/23222, Nature, 389, 990-994 (1997) and WO 99/64011; heterocyclic amino derivatives disclosed in WO 2001/56988; indazole derivatives disclosed in WO 2002/100833 and WO 2005/035506; and quinazoline derivatives disclosed in WO 2002/076976 and WO 2002/076977.

It has also been disclosed in Patent WO 2005/035506, WO 2000/09162 and WO 2000/57914 that a Rho kinase inhibitor is useful as a therapeutic agent for glaucoma.

However, in any of the above-mentioned documents, there is no specific disclosure for the indazole derivative having a spiro ring structure in a side chain according to the present invention.

DISCLOSURE OF THE INVENTION

Problems that the Invention is to Solve

It is a very interesting object to create a novel indazole derivative having a spiro ring structure in a side chain, which is useful as a pharmaceutical, and to find a new pharmacological activity of the derivative.

Means for Solving the Problems

In order to achieve the above object, the present inventors made synthetic studies for a novel indazole derivative having a spiro ring structure in a side chain (hereinafter referred to as the present indazole derivative) and succeeded in creating the novel compound.

Further, when the usefulness of the present indazole derivative as a pharmaceutical was variously investigated, it was found that the present indazole derivative has a Rho kinase inhibitory activity and is useful as a therapeutic agent for diseases associated with Rho kinase.

Further, in order to verify the application of the present indazole derivative to specific diseases associated with Rho kinase, an intraocular pressure-reducing activity of the present indazole derivative was also studied. As a result, it was found that the present indazole derivative has an excellent intraocular pressure-reducing activity and is useful as a therapeutic agent for eye diseases such as glaucoma, and thus, the present invention has been achieved.

The present invention relates to a compound represented by the following general formula [I] or a salt thereof (hereinafter, referred to as "the present invention compound" unless otherwise stated) and a pharmaceutical composition containing the present invention compound. In particular, the present invention relates to a Rho kinase inhibitor comprising the present invention compound as an active ingredient, and more particularly, it relates to a therapeutic agent for eye diseases such as glaucoma.

The present invention compound has a chemical structural feature in that it has a substituent having a spiro ring structure in a side chain of the ring X as shown in the following general formula [I].

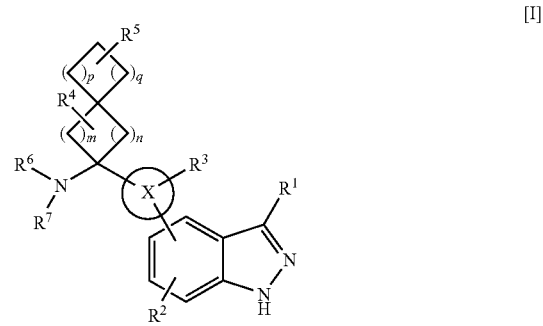

[In the formula, the ring X represents a benzene ring or a pyridine ring;

$R^1$ and $R^2$ are the same or different and represent one or plural groups selected from the group consisting of a halogen atom, a hydrogen atom, a hydroxy group, a substituted or unsubstituted alkoxy group, a substituted or unsubstituted alkenyloxy group, a substituted or unsubstituted alkynyloxy group, a substituted or unsubstituted cycloalkyloxy group, a substituted or unsubstituted cycloalkenyloxy group, a substituted or unsubstituted aryloxy group, a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted aryl group, a carboxy group or an ester or an amide thereof, a hydrocarbonyl group, a substituted or unsubstituted alkylcarbonyl group, a substituted or unsubstituted arylcarbonyl group, an amino group, a substituted or unsubstituted alkylamino group, a substituted or unsubstituted arylamino group, a mercapto group, a substituted or unsubstituted alkylthio group, a substituted or unsubstituted arylthio group, a sulfinic acid group or an ester or an amide thereof, a hydrosulfinyl group, a substituted or unsubstituted alkylsulfinyl group, a substituted or unsubstituted arylsulfinyl group, a sulfonic acid group or an ester or an amide thereof, a hydrosulfonyl group, a substituted or unsubstituted alkylsulfonyl group, a substituted or unsubstituted arylsulfonyl group, a nitro group, a cyano group and a substituted or unsubstituted monocyclic heterocyclic ring;

$R^3$ represents one or plural groups selected from the group consisting of a halogen atom, a hydrogen atom, a hydroxy group, a substituted or unsubstituted alkoxy group, a substituted or unsubstituted aryloxy group, a substituted or unsubstituted alkyl group and a substituted or unsubstituted aryl group;

$R^4$ and $R^5$ are the same or different and represent one or plural groups selected from the group consisting of a halogen atom, a hydrogen atom and a substituted or unsubstituted alkyl group;

$R^6$ and $R^7$ are the same or different and represent a group selected from the group consisting of a hydrogen atom, a substituted or unsubstituted alkyl group and a substituted or unsubstituted aryl group;

$R^6$ and $R^7$ may be joined together to form a monocyclic heterocyclic ring; and m, n, p and q are the same or different and represent an integer of 0 to 3, with the proviso that the sum of m and n is an integer of 1 or more and the sum of p and q is an integer of 1 or more. Hereinafter, the same shall apply.]

Advantage of the Invention

The present invention provides a novel indazole derivative having a spiro ring structure in a side chain or a salt thereof, which is useful as a pharmaceutical. The indazole derivative according to the present invention has an excellent Rho kinase inhibitory activity and is expected to be useful as a therapeutic agent for diseases associated with Rho kinase such as hypertension, angina pectoris, asthma, peripheral circular disorder, premature delivery, arteriosclerosis, cancer, inflammatory diseases, autoimmune diseases, AIDS, fertilization and implantation of a fertilized egg, osteoporosis, brain dysfunction, gastrointestinal dysfunction by bacteria, glaucoma and retinopathy.

BEST MODE FOR CARRYING OUT THE INVENTION

Each of the rings, atoms or groups which are defined in the present description will be described in detail as hereunder.

A "cycloalkane ring" refers to a cycloalkane ring having 3 to 8 carbon atoms. Specific examples thereof include cyclopropane, cyclobutane, cyclopentane, cyclohexane, cycloheptane and cyclooctane.

The "monocyclic heterocyclic ring" refers to a saturated or unsaturated monocyclic heterocyclic ring having one or plural hetero atoms selected from a nitrogen atom, an oxygen atom and a sulfur atom in the ring.

Specific examples of the saturated monocyclic heterocyclic ring include pyrrolidine, pyrazolidine, imidazolidine, triazolidine, piperidine, hexahydropyridazine, hexahydropyrimidine, piperazine, homopiperidine and homopiperazine, each of which has a nitrogen atom in the ring; tetrahydrofuran and tetrahydropyran, each of which has an oxygen atom in the ring; tetrahydrothiophene and tetrahydrothiopyran, each of which has a sulfur atom in the ring; oxazolidine, isoxazolidine and morpholine, each of which has a nitrogen atom and an oxygen atom in the ring; and thiazolidine, isothiazolidine and thiomorpholine, each of which has a nitrogen atom and a sulfur atom in the ring.

Specific examples of the unsaturated monocyclic heterocyclic ring include dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine and pyrazine, each of which has a nitrogen atom in the ring; dihydrofuran, furan, dihydropyran and pyran, each of which has an oxygen atom in the ring; dihydrothiophene, thiophene, dihydrothiopyran and thiopyran, each of which has a sulfur atom in the ring; dihydrooxazole, oxazole, dihydroisoxazole, isoxazole, dihydrooxazine and oxazine, each of which has a nitrogen atom and an oxygen atom in the ring; and dihydrothiazole, thiazole, dihydroisothiazole, isothiazole, dihydrothiazine and thiazine, each of which has a nitrogen atom and a sulfur atom in the ring.

The "halogen atom" refers to fluorine, chlorine, bromine or iodine.

The "alkoxy" refers to straight-chain or branched alkoxy having 1 to 6 carbon atoms. Specific examples thereof include methoxy, ethoxy, n-propoxy, n-butoxy, n-pentoxy, n-hexyloxy, isopropoxy, isobutoxy, sec-butoxy, tert-butoxy and isopentoxy.

The "alkenyloxy" refers to straight-chain or branched alkenyloxy having 2 to 8 carbon atoms. Specific examples thereof include vinyloxy, allyloxy, 1-propenyloxy, 3-butenyloxy, 3-pentenyloxy, 4-hexenyloxy, 5-heptenyloxy, 7-octenyloxy and 1-methylvinyloxy.

The "alkynyloxy" refers to straight-chain or branched alkynyloxy having 2 to 8 carbon atoms. Specific examples thereof include ethynyloxy, 2-propynyloxy, 2-butynyloxy, 3-pentynyloxy, 4-hexynyloxy, 5-heptynyloxy, 7-octynyloxy and 2-methylbutynyloxy.

The "cycloalkyloxy" refers to cycloalkyloxy having 3 to 8 carbon atoms. Specific examples thereof include cyclopropyloxy, cyclobutyloxy, cyclopentyloxy, cyclohexyloxy, cycloheptyloxy and cyclooctyloxy.

The "cycloalkenyloxy" refers to cycloalkenyloxy having 3 to 8 carbon atoms. Specific examples thereof include cyclopropenyloxy, cyclobutenyloxy, cyclopentenyloxy, cyclohexenyloxy, cycloheptenyloxy and cyclooctenyloxy.

The "aryloxy" refers to monocyclic aromatic hydrocarbonoxy or bicyclic or tricyclic condensed polycyclic aromatic hydrocarbonoxy having 6 to 14 carbon atoms. Specific examples thereof include phenoxy, naphthyloxy, anthryloxy and phenanthryloxy.

The "alkyl" refers to straight-chain or branched alkyl having 1 to 6 carbon atoms. Specific examples thereof include methyl, ethyl, n-propyl, n-butyl, n-pentyl, n-hexyl, isopropyl, isobutyl, sec-butyl, tert-butyl and isopentyl.

The "alkenyl" refers to straight-chain or branched alkenyl having 2 to 8 carbon atoms. Specific examples thereof include vinyl, allyl, 1-propenyl, 3-butenyl, 3-pentenyl, 4-hexenyl, 5-heptenyl, 7-octenyl and 1-methylvinyl.

The "alkynyl" refers to straight-chain or branched alkynyl having 2 to 8 carbon atoms. Specific examples thereof include ethynyl, 2-propynyl, 2-butynyl, 3-pentynyl, 4-hexynyl, 5-heptynyl, 7-octynyl and 2-methylbutynyl.

The "cycloalkyl" refers to cycloalkyl having 3 to 8 carbon atoms. Specific examples thereof include cyclopropyl, cyclobutyl, cyclopentyl, cyclohexyl, cycloheptyl and cyclooctyl.

The "cycloalkenyl" refers to cycloalkenyl having 3 to 8 carbon atoms. Specific examples thereof include cyclopropenyl, cyclobutenyl, cyclopentenyl, cyclohexenyl, cycloheptenyl and cyclooctenyl.

The "aryl" refers to a monocyclic aromatic hydrocarbon, or a bicyclic or tricyclic condensed polycyclic aromatic hydrocarbon having 6 to 14 carbon atoms. Specific examples thereof include phenyl, naphthyl, anthryl and phenanthryl.

The "ester of a carboxy group" refers to an ester composed of a carboxy group and an alkyl alcohol, an aryl alcohol or the like. Specific examples of the alkyl alcohol include methanol, ethanol, propanol and butanol, and specific examples of the aryl alcohol include phenol and naphthol.

The "amide of a carboxy group" refers to an amide composed of a carboxy group and ammonia, a primary or secondary amine or the like. The amine can be either an alkylamine or an arylamine and specific examples of the alkylamine include methylamine, ethylamine, ethylmethylamine, dimethylamine, diethylamine and dihexylamine, and specific examples of the arylamine include aniline, naphthylamine, methylphenylamine, ethylphenylamine and diphenylamine.

The "alkylcarbonyl" refers to straight-chain or branched alkylcarbonyl having 2 to 7 carbon atoms. Specific examples thereof include methylcarbonyl, ethylcarbonyl, n-propylcarbonyl, n-butylcarbonyl, n-pentylcarbonyl, n-hexylcarbonyl, isopropylcarbonyl, isobutylcarbonyl, sec-butylcarbonyl, tert-butylcarbonyl and isopentylcarbonyl.

The "arylcarbonyl" refers to monocyclic aromatic hydrocarbon carbonyl or bicyclic or tricyclic condensed polycyclic aromatic hydrocarbon carbonyl having 7 to 15 carbon atoms. Specific examples thereof include phenylcarbonyl, naphthylcarbonyl, anthrylcarbonyl and phenanthrylcarbonyl.

The "alkylamino" refers to mono- or dialkylamino. Specific examples thereof include methylamino, ethylamino, ethylmethylamino, dimethylamino, diethylamino and dihexylamino.

The "arylamino" refers to mono- or diarylamino. Specific examples thereof include phenylamino, naphthylamino, methylphenylamino, ethylphenylamino and diphenylamino.

The "alkylthio" refers to straight-chain or branched alkylthio having 1 to 6 carbon atoms. Specific examples thereof include methylthio, ethylthio, n-propylthio, n-butylthio, n-pentylthio, n-hexylthio, isopropylthio, isobutylthio, sec-butylthio, tert-butylthio and isopentylthio.

The "arylthio" refers to monocyclic aromatic hydrocarbonthio or bicyclic or tricyclic condensed polycyclic aromatic hydrocarbonthio having 6 to 14 carbon atoms. Specific examples thereof include phenylthio, naphthylthio, anthrylthio and phenanthrylthio.

The "ester of a sulfinic acid group" refers to an ester composed of a sulfinic acid group and an alkyl alcohol, an aryl alcohol or the like. Specific examples of the alkyl alcohol include methanol, ethanol, propanol and butanol, and specific examples of the aryl alcohol include phenol and naphthol.

The "amide of a sulfinic acid group" refers to an amide composed of a sulfinic acid group and ammonia, a primary or secondary amine or the like. The amine can be either an alkylamine or an arylamine and specific examples of the alkylamine include methylamine, ethylamine, ethylmethylamine, dimethylamine, diethylamine and dihexylamine, and specific examples of the arylamine include aniline, naphthylamine, methylphenylamine, ethylphenylamine and diphenylamine.

The "alkylsulfinyl" refers to straight-chain or branched alkylsulfinyl having 1 to 6 carbon atoms. Specific examples thereof include methylsulfinyl, ethylsulfinyl, n-propylsulfinyl, n-butylsulfinyl, n-pentylsulfinyl, n-hexylsulfinyl, isopropylsulfinyl, isobutylsulfinyl, sec-butylsulfinyl, tert-butylsulfinyl and isopentylsulfinyl.

The "arylsulfinyl" refers to monocyclic aromatic hydrocarbon sulfinyl or bicyclic or tricyclic condensed polycyclic aromatic hydrocarbon sulfinyl having 6 to 14 carbon atoms. Specific examples thereof include phenylsulfinyl, naphthylsulfinyl, anthrylsulfinyl and phenanthrylsulfinyl.

The "ester of a sulfonic acid group" refers to an ester composed of a sulfonic acid group and an alkyl alcohol, an aryl alcohol or the like. Specific examples of the alkyl alcohol include methanol, ethanol, propanol and butanol, and specific examples of the aryl alcohol include phenol and naphthol.

The "amide of a sulfonic acid group" refers to an amide composed of a sulfonic acid group and ammonia, a primary or secondary amine or the like. The amine may be either an alkylamine or an arylamine and specific examples of the alkylamine include methylamine, ethylamine, ethylmethylamine, dimethylamine, diethylamine and dihexylamine, and specific examples of the arylamine include aniline, naphthylamine, methylphenylamine, ethylphenylamine and diphenylamine.

The "alkylsulfonyl" refers to straight-chain or branched alkylsulfonyl having 1 to 6 carbon atoms. Specific examples thereof include methylsulfonyl, ethylsulfonyl, n-propylsulfonyl, n-butylsulfonyl, n-pentylsulfonyl, n-hexylsulfonyl, isopropylsulfonyl, isobutylsulfonyl, sec-butylsulfonyl, tert-butylsulfonyl and isopentylsulfonyl.

The "arylsulfonyl" refers to monocyclic aromatic hydrocarbon sulfonyl or bicyclic or tricyclic condensed polycyclic aromatic hydrocarbon sulfonyl having 6 to 14 carbon atoms. Specific examples thereof include phenylsulfonyl, naphthylsulfonyl, anthrylsulfonyl and phenanthrylsulfonyl.

The "alkoxyimino" refers to straight-chain or branched alkoxyimino having 1 to 6 carbon atoms. Specific examples thereof include methoxyimino, ethoxyimino, n-propoxyimino, n-butoxyimino, n-pentoxyimino, n-hexyloxyimino, isopropoxyimino, isobutoxyimino, sec-butoxyimino, tert-butoxyimino and isopentoxyimino.

The "aryloxyimino" refers to monocyclic aromatic hydrocarbon oxyimino or bicyclic or tricyclic condensed polycyclic aromatic hydrocarbon oxyimino having 6 to 14 carbon atoms. Specific examples thereof include phenoxyimino, naphthyloxyimino, anthryloxyimino and phenanthryloxyimino.

A "substituted cycloalkane ring" refers to a cycloalkane ring having one or plural groups selected from a halogen atom, a hydroxy group, an alkoxy group, an aryloxy group, an alkyl group, a cycloalkyl group, an aryl group, a carboxy group or an ester or an amide thereof, an amino group, an alkylamino group, an arylamino group, a nitro group and a cyano group as substituents.

The "substituted monocyclic heterocyclic ring" refers to a monocyclic heterocyclic group in which a carbon atom moiety thereof has one or plural groups selected from a halogen atom, a hydroxy group, an alkoxy group, an aryloxy group, an alkyl group, a cycloalkyl group, an aryl group, a carboxy group or an ester or an amide thereof, an amino group, an alkylamino group, an arylamino group, a mercapto group, an alkylthio group, an arylthio group, a hydrocarbonyl group, i.e., a formyl group, an alkylcarbonyl group, an arylcarbonyl group, a nitro group and a cyano group as substituents.

The "substituted alkoxy group" refers to an alkoxy group having one or plural groups selected from a halogen atom, a hydroxy group, an alkoxy group, an aryloxy group, a cycloalkyl group, an aryl group, an aryl group substituted with a halogen atom, an aryl group substituted with an alkoxy group, a carboxy group or an ester or an amide thereof, an amino group, an alkylamino group, an arylamino group, a nitro group, a cyano group, a hydroxyimino group, an alkoxyimino group and an aryloxyimino group as substituents.

The "substituted alkenyloxy group" refers to an alkenyloxy group having one or plural groups selected from a halogen atom, a hydroxy group, an alkoxy group, an aryloxy group, a cycloalkyl group, an aryl group, an aryl group substituted with a halogen atom, an aryl group substituted with an alkoxy group, a carboxy group or an ester or an amide thereof, an amino group, an alkylamino group, an arylamino group, a nitro group and a cyano group as substituents.

The "substituted alkynyloxy group" refers to an alkynyloxy group having one or plural groups selected from a halogen atom, a hydroxy group, an alkoxy group, an aryloxy group, a cycloalkyl group, an aryl group, an aryl group substituted with a halogen atom, an aryl group substituted with an alkoxy group, a carboxy group or an ester or an amide thereof, an amino group, an alkylamino group, an arylamino group, a nitro group and a cyano group as substituents.

The "substituted cycloalkyloxy group" refers to a cycloalkyloxy group having one or plural groups selected from a halogen atom, a hydroxy group, an alkoxy group, an aryloxy group, an alkyl group, a cycloalkyl group, an aryl group, a carboxy group or an ester or an amide thereof, an amino group, an alkylamino group, an arylamino group, a nitro group and a cyano group as substituents.

The "substituted cycloalkenyloxy group" refers to a cycloalkenyloxy group having one or plural groups selected from a halogen atom, a hydroxy group, an alkoxy group, an aryloxy group, an alkyl group, a cycloalkyl group, an aryl group, a carboxy group or an ester or an amide thereof, an amino group, an alkylamino group, an arylamino group, a nitro group and a cyano group as substituents.

The "substituted aryloxy group" refers to an aryloxy group having one or plural groups selected from a halogen atom, a hydroxy group, an alkoxy group, an aryloxy group, an alkyl group, a cycloalkyl group, an aryl group, a carboxy group or an ester or an amide thereof, an amino group, an alkylamino group, an arylamino group, a nitro group and a cyano group as substituents.

The "substituted alkyl group" refers to an alkyl group having one or plural groups selected from a halogen atom, a hydroxy group, an alkoxy group, an aryloxy group, a cycloalkyl group, an aryl group, an aryl group substituted with a halogen atom, an aryl group substituted with an alkoxy group, a carboxy group or an ester or an amide thereof, an amino group, an alkylamino group, an arylamino group, a nitro group, a cyano group, a hydroxyimino group, an alkoxyimino group and an aryloxyimino group as substituents.

The "substituted alkenyl group" refers to an alkenyl group having one or plural groups selected from a halogen atom, a hydroxy group, an alkoxy group, an aryloxy group, a cycloalkyl group, an aryl group, an aryl group substituted with a halogen atom, an aryl group substituted with an alkoxy group, a carboxy group or an ester or an amide thereof, an amino group, an alkylamino group, an arylamino group, a nitro group, a cyano group, a hydroxyimino group, an alkoxyimino group and an aryloxyimino group as substituents.

The "substituted alkynyl group" refers to an alkynyl group having one or plural groups selected from a halogen atom, a hydroxy group, an alkoxy group, an aryloxy group, a cycloalkyl group, an aryl group, an aryl group substituted with a halogen atom, an aryl group substituted with an alkoxy group, a carboxy group or an ester or an amide thereof, an amino group, an alkylamino group, an arylamino group, a nitro group and a cyano group as substituents.

The "substituted cycloalkyl group" refers to a cycloalkyl group having one or plural groups selected from a halogen atom, a hydroxy group, an alkoxy group, an aryloxy group, an alkyl group, a cycloalkyl group, an aryl group, a carboxy group or an ester or an amide thereof, an amino group, an alkylamino group, an arylamino group, a nitro group and a cyano group as substituents.

The "substituted cycloalkenyl group" refers to a cycloalkenyl group having one or plural groups selected from a halogen atom, a hydroxy group, an alkoxy group, an aryloxy group, an alkyl group, a cycloalkyl group, an aryl group, a carboxy group or an ester or an amide thereof, an amino group, an alkylamino group, an arylamino group, a nitro group and a cyano group as substituents.

The "substituted aryl group" refers to an aryl group having one or plural groups selected from a halogen atom, a hydroxy group, an alkoxy group, an aryloxy group, an alkyl group, a cycloalkyl group, an aryl group, a carboxy group or an ester or an amide thereof, an amino group, an alkylamino group, an arylamino group, a nitro group, a cyano group, a hydroxyimino group, an alkoxyimino group and an aryloxyimino group as substituents.

The "substituted alkylcarbonyl group" refers to an alkylcarbonyl group having one or plural groups selected from a halogen atom, a hydroxy group, an alkoxy group, an aryloxy group, a cycloalkyl group, an aryl group, an aryl group substituted with a halogen atom, an aryl group substituted with an alkoxy group, a carboxy group or an ester or an amide thereof, an amino group, an alkylamino group, an arylamino group, a nitro group and a cyano group as substituents.

The "substituted arylcarbonyl group" refers to an arylcarbonyl group having one or plural groups selected from a halogen atom, a hydroxy group, an alkoxy group, an aryloxy group, an alkyl group, a cycloalkyl group, an aryl group, a carboxy group or an ester or an amide thereof, an amino group, an alkylamino group, an arylamino group, a nitro group and a cyano group as substituents.

The "substituted alkylamino group" refers to an alkylamino group in which an alkyl moiety thereof has one or plural groups selected from a halogen atom, a hydroxy group, an alkoxy group, an aryloxy group, a cycloalkyl group, an aryl group, an aryl group substituted with a halogen atom, an aryl group substituted with an alkoxy group, a carboxy group or an ester or an amide thereof, an amino group, an alkylamino group, an arylamino group, a nitro group and a cyano group as substituents.

The "substituted arylamino group" refers to an arylamino group in which an aryl moiety thereof has one or plural groups selected from a halogen atom, a hydroxy group, an alkoxy group, an aryloxy group, an alkyl group, a cycloalkyl group, an aryl group, a carboxy group or an ester or an amide thereof, an amino group, an alkylamino group, an arylamino group, a nitro group and a cyano group as substituents.

The "substituted alkylthio group" refers to an alkylthio group having one or plural groups selected from a halogen atom, a hydroxy group, an alkoxy group, an aryloxy group, a cycloalkyl group, an aryl group, an aryl group substituted with a halogen atom, an aryl group substituted with an alkoxy group, a carboxy group or an ester or an amide thereof, an amino group, an alkylamino group, an arylamino group, a nitro group and a cyano group as substituents.

The "substituted arylthio group" refers to an arylthio group having one or plural groups selected from a halogen atom, a hydroxy group, an alkoxy group, an aryloxy group, an alkyl group, a cycloalkyl group, an aryl group, a carboxy group or an ester or an amide thereof, an amino group, an alkylamino group, an arylamino group, a nitro group and a cyano group as substituents.

The "substituted alkylsulfinyl group" refers to an alkylsulfinyl group having one or plural groups selected from a halogen atom, a hydroxy group, an alkoxy group, an aryloxy group, a cycloalkyl group, an aryl group, an aryl group substituted with a halogen atom, an aryl group substituted with an alkoxy group, a carboxy group or an ester or an amide thereof, an amino group, an alkylamino group, an arylamino group, a nitro group and a cyano group as substituents.

The "substituted arylsulfinyl group" refers to an arylsulfinyl group having one or plural groups selected from a halogen atom, a hydroxy group, an alkoxy group, an aryloxy group, an alkyl group, a cycloalkyl group, an aryl group, a carboxy group or an ester or an amide thereof, an amino group, an alkylamino group, an arylamino group, a nitro group and a cyano group as substituents.

The "substituted alkylsulfonyl group" refers to an alkylsulfonyl group having one or plural groups selected from a halogen atom, a hydroxy group, an alkoxy group, an aryloxy group, a cycloalkyl group, an aryl group, an aryl group substituted with a halogen atom, an aryl group substituted with an alkoxy group, a carboxy group or an ester or an amide thereof, an amino group, an alkylamino group, an arylamino group, a nitro group and a cyano group as substituents.

The "substituted arylsulfonyl group" refers to an arylsulfonyl group having one or plural groups selected from a halogen atom, a hydroxy group, an alkoxy group, an aryloxy group, an alkyl group, a cycloalkyl group, an aryl group, a carboxy group or an ester or an amide thereof, an amino group, an alkylamino group, an arylamino group, a nitro group and a cyano group as substituents.

When the present invention compound has a free hydroxy group, amino group, alkylamino group or arylamino group as a substituent, such a group may be protected by a protecting group.

The protecting group for a free hydroxy group refers to a protecting group commonly used as a protecting group for a free hydroxy group, and examples thereof include a substituted or unsubstituted alkyl group or an unsubstituted alkenyl group such as a methoxymethyl group, a benzyl group, a trityl group, a 4-methoxyphenylmethyl group, a benzyloxymethyl group, a methyl group and an allyl group; a substituted or unsubstituted heterocyclic group such as a 3-bromotetrahydropyranyl group, a tetrahydropyranyl group and a tetrahydrofuranyl group; a substituted or unsubstituted alkylcarbonyl group or a substituted or unsubstituted arylcarbonyl group such as a trifluoroacetyl group, an acetyl group, a 4-chlorobenzoyl group and a benzoyl group; a substituted or unsubstituted alkyloxycarbonyl group, an unsubstituted alkenyloxycarbonyl group or a substituted or unsubstituted aryloxycarbonyl group such as a benzyloxycarbonyl group, a 4-methoxybenzyloxycarbonyl group, a 9-fluorenylmethoxycarbonyl group, a methoxycarbonyl group, an ethoxycarbonyl group, an isobutoxycarbonyl group, a tert-butoxycarbonyl group, a vinyloxycarbonyl group, an allyloxycarbonyl group, a 4-nitrophenoxycarbonyl group and a phenoxycarbonyl group; and a substituted silyl group such as a trimethylsilyl group, a triethylsilyl group, a triisopropylsilyl group, a tert-butyldimethylsilyl group and a tert-butyldiphenylsilyl group.

The protecting group for a free amino group, alkylamino group or arylamino group refers to a protecting group commonly used as a protecting group for a free amino group, alkylamino group or arylamino group, and examples thereof include a substituted alkyl group or an unsubstituted alkenyl group such as a benzyl group, a trityl group, a diphenylmethyl group, a (4-methoxyphenyl)diphenylmethyl group and an allyl group; a hydrocarbonyl group, i.e., a formyl group; a substituted or unsubstituted alkylcarbonyl group, a substituted or unsubstituted arylcarbonyl group or an unsubstituted heterocyclic carbonyl group such as a trichloroacetyl group, a trifluoroacetyl group, an acetyl group, a 4-chlorobenzoyl group, a benzoyl group and a picolinoyl group; a substituted or unsubstituted alkyloxycarbonyl group or a substituted or unsubstituted aryloxycarbonyl group such as a 2,2,2-trichloroethoxycarbonyl group, a benzyloxycarbonyl group, a diphenylmethoxycarbonyl group, a methoxycarbonyl group, an isobutoxycarbonyl group, a tert-butoxycarbonyl group, a 3-nitrophenoxycarbonyl group and a phenoxycarbonyl group; and a substituted or unsubstituted alkylsulfonyl group or a substituted or unsubstituted arylsulfonyl group such as a benzylsulfonyl group, a tolylsulfonyl group, a methylsulfonyl group, a 4-chlorophenylsulfonyl group, a 2,4,6-trimethylphenylsulfonyl group and a phenylsulfonyl group.

The nitrogen atom of the indazole ring of the present invention compound may be protected with a protecting group.

The protecting group for a nitrogen atom of the indazole ring refers to a protecting group commonly used as a protecting group for a nitrogen atom of the indazole ring, and examples thereof include a substituted alkyl group or an unsubstituted alkenyl group such as a benzyl group, a trityl group, a diphenylmethyl group, a (4-methoxyphenyl)diphenylmethyl group and an allyl group; a hydrocarbonyl group, i.e., a formyl group; a substituted or unsubstituted alkylcarbonyl group, a substituted or unsubstituted arylcarbonyl group or an unsubstituted heterocyclic carbonyl group such as a trichloroacetyl group, a trifluoroacetyl group, an acetyl group, a 4-chlorobenzoyl group, a benzoyl group and a picolinoyl group; a substituted or unsubstituted alkyloxycarbonyl group or a substituted or unsubstituted aryloxycarbonyl group such as a 2,2,2-trichloroethoxycarbonyl group, a benzyloxycarbonyl group, a diphenylmethoxycarbonyl group, a methoxycarbonyl group, an isobutoxycarbonyl group, a tert-butoxycarbonyl group, a phenoxycarbonyl group and a 3-nitrophenoxycarbonyl group; and a substituted or unsubstituted alkylsulfonyl group or a substituted or unsubstituted arylsulfonyl group such as a benzylsulfonyl group, a tolylsulfonyl group, a methylsulfonyl group, a 4-chlorophenylsulfonyl group, a 2,4,6-trimethylphenylsulfonyl group and a phenylsulfonyl group.

The "salt" of the present invention compound is not particularly limited as long as it is a pharmaceutically acceptable salt, and examples thereof include a salt with an inorganic acid such as hydrochloric acid, hydrobromic acid, hydroiodic acid, nitric acid, sulfuric acid or phosphoric acid; a salt with an organic acid such as acetic acid, fumaric acid, maleic acid, succinic acid, citric acid, tartaric acid, adipic acid, lactic acid, methanesulfonic acid, trifluoromethanesulfonic acid, p-toluenesulfonic acid or trifluoroacetic acid; a salt with an alkali metal such as lithium, sodium or potassium; a salt with an alkaline earth metal such as calcium or magnesium; and a quaternary salt with ammonia, methyl iodide or the like.

With regard to the term "plural groups" in the present invention, the respective groups may be the same or different from one another. In the case of $R^2$, the term means 2 to 3 groups, in the case of $R^3$, the term means 2 to 4 groups, and in the case of $R^4$ and $R^5$, the term means 2 to 12 groups. Further, a halogen atom, a hydrogen atom and a monocyclic heterocyclic ring are also included in the "group".

When there are geometric isomers such as syn-anti isomers or optical isomers in the present invention compound, such isomers are also included in the scope of the present invention.

Further, the present invention compound can also be in the form of a hydrate or a solvate.

Preferred examples of the present invention compound defined as described above by the general formula [I] include compounds, in which the above-mentioned substituted alkoxy group, substituted alkyl group, substituted alkenyl group and/or substituted aryl group have/has been substituted with one or plural groups selected from the group consisting of a halogen atom, a hydroxy group, an unsubstituted alkoxy group, an unsubstituted aryl group, a hydroxyimino group and an unsubstituted alkoxyimino group, and salts thereof.

Other preferred examples of the present invention compound defined as described above by the general formula [I] include compounds which are defined by one or two or more combinations of the following seven alternatives i) to vii) and salts thereof:

i) the ring X represents a benzene ring or a pyridine ring;
ii) $R^1$ represents a hydrogen atom, a substituted alkyl group, an unsubstituted alkenyl group, a carboxy group or an ester or an amide thereof, an amino group or a cyano group;
iii) $R^2$ represents a hydrogen atom, a hydroxy group, a substituted or unsubstituted alkoxy group, an unsubstituted alkenyloxy group, an unsubstituted cycloalkyloxy group, a substituted or unsubstituted alkyl group, an unsubstituted alkenyl group, an unsubstituted cycloalkyl group, an amino group, an unsubstituted alkylamino group, a nitro group, a cyano group or a monocyclic heterocyclic group;
iv) $R^3$ represents a halogen atom or a hydrogen atom;
v) $R^4$ and $R^5$ represent a hydrogen atom;
vi) $R^6$ and $R^7$ represent a hydrogen atom; and
vii) m, n, p and q are the same or different and represent an integer of 0 to 2, with the proviso that the sum of m and n is an integer of 1 or more and the sum of p and q is an integer of 1 or more.

Among them, more preferred examples of the present invention compound include compounds which are defined by one or two or more combinations of the following five alternatives i) to v) and salts thereof:

i) the ring X represents a pyridine ring;
ii) $R^1$, $R^3$, $R^4$, $R^5$, $R^6$ and $R^7$ represent a hydrogen atom;
iii) $R^2$ represents an unsubstituted cycloalkyl group;
iv) m and n represent 1; and
v) one of p and q represents 0 and the other represents 1.

Other preferred examples of the present invention compound defined as described above by the general formula [I] include compounds, in which the substituted alkoxy group has been substituted with a halogen atom and/or the substituted alkyl group has been substituted with one or plural groups selected from the group consisting of a hydroxy group and a hydroxyimino group, and salts thereof.

More preferred examples of the present invention compound defined as described above by the general formula [I] include compounds, which are defined by one or two or more combinations of the following eight alternatives i) to viii) and salts thereof:

i) the ring X represents a benzene ring or a pyridine ring;
ii) $R^1$ represents a hydrogen atom, a hydroxymethyl group, a hydroxyiminomethyl group, a 1-methylvinyl group, a carboxy group, a methoxycarbonyl group, an aminocarbonyl group, an amino group or a cyano group;
iii) $R^2$ represents a hydrogen atom, a hydroxy group, a methoxy group, an ethoxy group, an n-propyloxy group, an n-butyloxy group, an isopropyloxy group, a difluoromethoxy group, a 2-fluoroethoxy group, a 2,2,2-trifluoroethoxy group, an allyloxy group, a cyclopropyloxy group, a cyclopropylmethyloxy group, an ethyl group, a vinyl group, a hydroxymethyl group, a 1-hydroxyethyl group, a 2-hydroxyethyl group, a cyclopropyl group, a cyclobutyl group, a cyclopentyl group, a cyclohexyl group, an amino group, a methylamino group, a dimethylamino group, a diethylamino group, a nitro group, a cyano group, a pyrrolidine ring, a pyrrole ring, a pyrazole ring, an oxazole ring, an isoxazole ring, a piperidine ring, a pyridine ring or a morpholine ring;
iv) $R^3$ represents a chlorine atom or a hydrogen atom;
v) $R^4$ and $R^5$ represent a hydrogen atom;
vi) $R^6$ and $R^7$ represent a hydrogen atom;
vii) m and n represent 1; and
viii) one of p and q represents 0 and the other represents 1.

In the present invention compound defined as described above by the general formula [I], compounds, in which the ring X has been substituted at the 5-position of the indazole ring, and salts thereof are particularly preferred.

As described above, the present invention compound has a chemical structural feature in that it has a substituent having a spiro ring structure in a side chain of the ring X as shown in the general formula [I]. That is, the present invention compound in which
a) in the case where the ring X is a benzene ring, the following substituent of the general formula [I] is attached to the 4-position of the ring X; or
b) in the case where the ring X is a pyridine ring, the following substituent of the general formula [I] is attached to the 5-position of the ring X is particularly preferred.

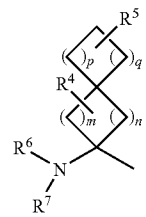

Particularly preferred specific examples of the present invention compound include compounds shown below and salts thereof.

5-{5-(1-amino-spiro[2,2]pent-1-yl)pyridin-2-yl}-4-cyclopropyl-1H-indazole

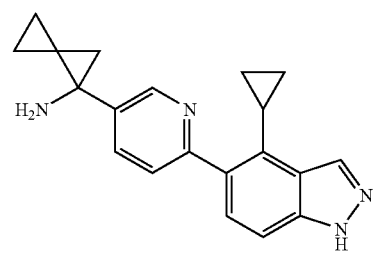

5-{5-(1-amino-spiro[2,3]hex-1-yl)pyridin-2-yl}-4-cyclopropyl-1H-indazole

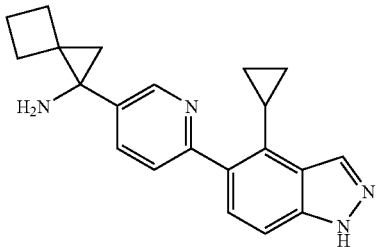

5-{5-(S-amino-spiro[2,3]hex-5-yl)pyridin-2-yl}-4-cyclopropyl-1H-indazole

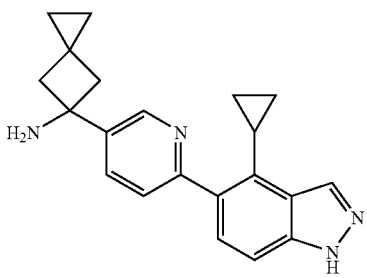

5-{4-(5-amino-spiro[2,3]hex-5-yl)phenyl}-4-cyclopropyl-1H-indazole

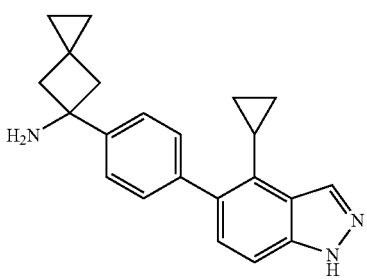

5-{5-(2-amino-spiro[3,3]hept-2-yl)pyridin-2-yl}-4-cyclopropyl-1H-indazole

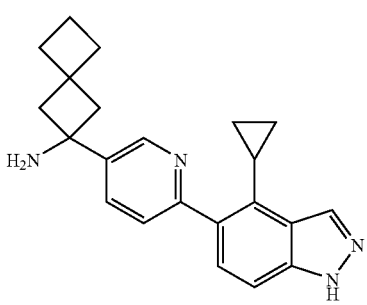

A representative method for producing the present invention compound will be shown below. Incidentally, specific methods for producing the respective present invention compounds will be described in detail in the "section of Production Examples" in the Examples which will be mentioned later.

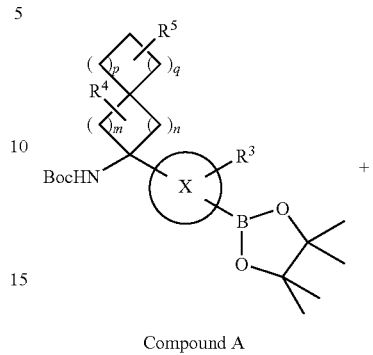

Compound A

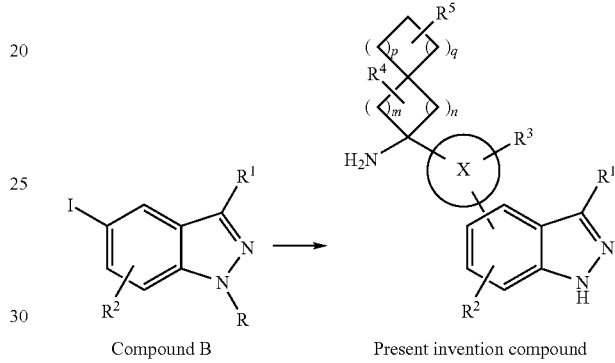

Synthetic pathway 2

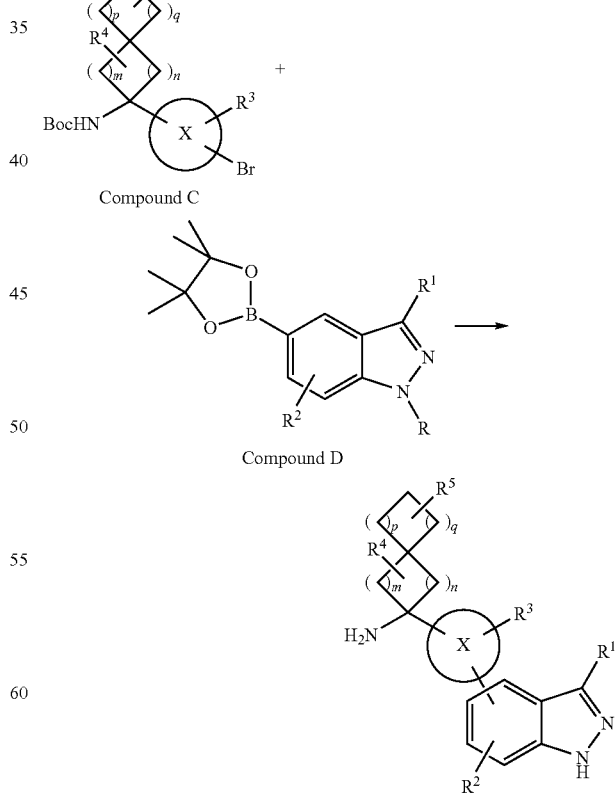

Synthetic pathway 1 or Synthetic pathway 2: Compound A and Compound B, or Compound C and Compound D are subjected to a coupling reaction in an organic solvent in the presence of a metal catalyst and/or a base, whereby the present invention compound can be obtained.

In the case where a protecting group is used for the convenience of the production in the above-mentioned production method, the protecting group can be removed by a commonly used method.

With regard to the substituent on the ring x and/or the indazole ring, a desired substituent may be introduced in its initial stage or it is also acceptable that, after a fundamental skeleton is formed by the above-mentioned method, a desired substituent may be introduced into the fundamental skeleton using oxidation, reduction, alkylation, esterification, amidation, oximation, dehydration reaction, deprotection reaction, acetylation, hydrolysis, triflation, coupling reaction, cyclization reaction and/or a commonly used synthetic method in which the above-mentioned reactions are combined.

A method for producing a synthetic intermediate of the present invention compound will be described in detail in the "section of Production Examples" in the Examples which will be mentioned later.

Further, such a synthetic intermediate can be produced in accordance with the method described in WO 2005/035506.

In order to find the usefulness of the present invention compound, a Rho kinase inhibitory activity of the present invention compound was evaluated and studied. The details of the evaluation and study will be illustrated in the "section of Pharmacological Test (Test for Evaluation of Rho Kinase Inhibitory Activity)" in the Examples which will be mentioned later. The evaluation and study of the Rho kinase inhibitory activity of the present invention compound were carried out in accordance with the method described in J. Biol. Chem., 274, 32418 (1999) and the method described in the instruction manual for use attached to the commercially available activated ROCK-II [Upstate Biotechnology, Catalog No. 14-338 (5 units/50 µl)]. As a result, it was found that the present invention compound has an excellent Rho kinase inhibitory activity and is very useful as a therapeutic agent for diseases associated with Rho kinase.

Further, in order to verify the application of the present invention compound to a specific disease associated with Rho kinase, the intraocular pressure-reducing activity of the present invention compound was also studied. The details of the study will be illustrated in the "section of Pharmacological Test (Test for Measurement of Intraocular Pressure-Reducing Activity)" in the Examples which will be mentioned later. When the present invention compound was administered by instillation to the eyes of cynomolgus monkeys (sex: male; one group consisting of 4 to 5 monkeys), it was found that the present invention compound has an excellent intraocular pressure-reducing activity and is also useful as a therapeutic agent for eye diseases such as glaucoma.

As described above, Rho kinase has been known to deeply participate in diseases such as hypertension, angina pectoris, asthma, peripheral circular disorder, premature delivery, arteriosclerosis, cancer, inflammatory diseases, autoimmune diseases, AIDS, fertilization and implantation of a fertilized egg, osteoporosis, brain dysfunction, gastrointestinal dysfunction by bacteria, glaucoma and retinopathy. Accordingly, the present invention compound is very much expected as a therapeutic agent for diseases associated with Rho kinase.

In addition, the Rho kinase inhibitor in the present invention means a compound which inhibits serine/threonine kinase which is activated as a result of activation of Rho.

Examples of glaucoma in the present invention include primary open angle glaucoma, normal tension glaucoma, hypersecretion glaucoma, ocular hypertension, acute angle-closure glaucoma, chronic angle-closure glaucoma, combined mechanism glaucoma, steroid glaucoma, amyloid glaucoma, neovascular glaucoma, malignant glaucoma, capsular glaucoma and plateau iris syndrome.

The present invention compound can be administered either orally or parenterally. Examples of the dosage form include tablets, capsules, granules, powders, injections and eye drops and they can be made into such pharmaceutical preparations by commonly used techniques in combination.

For example, an oral preparation such as a tablet, a capsule, a granule or a powder can be prepared by combining the present invention compound together, if necessary, with an excipient such as lactose, mannitol, starch, crystalline cellulose, light anhydrous silicic acid, calcium carbonate or calcium hydrogen phosphate; a lubricant such as stearic acid, magnesium stearate or talc; a binder such as starch (potato starch, corn starch, or the like), hydroxypropyl cellulose, hydroxymethyl cellulose or polyvinylpyrrolidone; a disintegrant such as carboxymethyl cellulose, carboxymethyl cellulose calcium, low-substituted hydroxypropylmethyl cellulose or calcium citrate; a coating agent such as hydroxypropylmethyl cellulose, macrogol or a silicone resin; a stabilizer such as ethyl p-hydroxybenzoate or benzyl alcohol; a corrigent such as a sweetener, a sour agent or a flavor; or the like.

A parenteral preparation such as an injection or an eye drop can be prepared by combining the present invention compound together, if necessary, with a tonicity agent such as glycerin, propylene glycol, sodium chloride, potassium chloride, sorbitol or mannitol; a buffer such as phosphoric acid, a phosphate, citric acid, glacial acetic acid, ε-aminocaproic acid or trometamol; a pH adjusting agent such as hydrochloric acid, citric acid, phosphoric acid, glacial acetic acid, sodium hydroxide, potassium hydroxide, sodium carbonate or sodium hydrogen carbonate; a solubilizer or a dispersant such as polysorbate 80, polyoxyethylene hydrogenated castor oil 60, macrogol 4000, purified soybean lecithin or polyoxyethylene (160) polyoxypropylene (30) glycol; a cellulosic polymer such as hydroxypropylmethyl cellulose or hydroxypropyl cellulose; a viscosity-increasing agent such as polyvinyl alcohol or polyvinylpyrrolidone; a stabilizer such as edetic acid or sodium edetate; a commonly used preservative or antiseptic such as sorbic acid, potassium sorbate, benzalkonium chloride, benzethonium chloride, methyl p-hydroxybenzoate, propyl p-hydroxybenzoate or chlorobutanol; a soothing agent such as chlorobutanol, benzyl alcohol or lidocaine; or the like.

In the case of an injection or an eye drop, it is desired that the pH is adjusted to 4.0 to 8.0 and that the osmotic pressure ratio is adjusted to about 1.0.

The present invention also relates to a method of inhibiting Rho kinase comprising administering an effective amount of the present invention compound or a salt thereof to a patient, and a method of treating glaucoma comprising administering an effective amount of the present invention compound or a salt thereof to a patient.

The dose of the present invention compound can be appropriately selected and used depending on the symptoms, age, dosage form and the like. For example, in the case of an oral preparation, usually 0.01 to 1000 mg per day, preferably 1 to 100 mg per day can be administered once or divided into several times a day.

Further, in the case of an eye drop, usually an eye drop containing the present invention compound at a concentration of from 0.0001% to 10% (w/v), preferably from 0.001% to 5% (w/v) can be administered once or divided into several times.

Hereinafter, Production Examples of the present invention compounds (Examples 1 to 2) and synthetic intermediates thereof (Reference Examples 1 to 9), Preparation Examples and Results of Pharmacological Tests will be described. However, these examples are described for the purpose of understanding the present invention better and are not meant to limit the scope of the present invention. Further, the Rf values in the physical properties of Examples are represented by the values measured using a thin-layer chromatography (manufactured by Merck Ltd., TLC plate silica gel 60F$_{254}$ (trade name)), and in the chemical structural formulae, Boc represents a tert-butoxycarbonyl group and THP represents a tetrahydropyranyl group unless otherwise specified.

Reference Example 1

Synthesis of 3-cyclopropyl-2-methylacetanilide (Reference Compound 1)

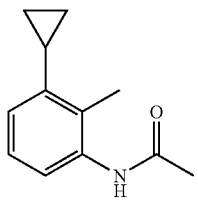

Under a nitrogen stream, 184 g (1.00 mol) of 3-chloro-2-methylacetanilide, 129 g (1.50 mol) of cyclopropylboronic acid, 745 g (3.00 mol) of potassium phosphate dihydrate, 120 ml of water, 63.0 ml (0.040 mol) of a 20% by weight solution of tricyclohexylphosphine in toluene and 4.49 g (0.020 mol) of palladium acetate were sequentially added to 2000 ml of toluene, and the resulting mixture was stirred with heating at 90° C. to 100° C. for 7 hours.

After the reaction was completed, the reaction solution was cooled to room temperature, and 1000 ml of water and 1000 ml of ethyl acetate were added thereto. Then, the resulting mixture was filtered through Celite (trade name) and the filtrate was subjected to liquid separation. The organic layer was sequentially washed with 1000 ml of water and 1000 ml of a saturated aqueous solution of sodium chloride, dried over anhydrous magnesium sulfate and concentrated under reduced pressure. To the resulting residue, 2000 ml of n-hexane was added, and the resulting solid was collected by filtration and dried, whereby 156 g of the title compound was obtained as a gray white solid (yield: 82%).

Melting point: 119-120° C.
Rf value: 0.25 (n-hexane:ethyl acetate=1:1 (v/v))
Mass spectrum (CI, m/z): 190 (M$^+$+1)
$^1$H-NMR spectrum (DMSO-d$_6$, δ ppm): 0.54-0.59 (m, 2H), 0.87-0.93 (m, 2H), 1.85-1.94 (m, 1H), 2.04 (s, 3H), 2.23 (s, 3H), 6.83 (d, J=7.3 Hz, 1H), 7.01-7.06 (m, 1H), 7.12 (d, J=7.3 Hz, 1H), 9.32 (brs, 1H)

Reference Example 2

Synthesis of 4-bromo-3-cyclopropyl-2-methylacetanilide (Reference Compound 2)

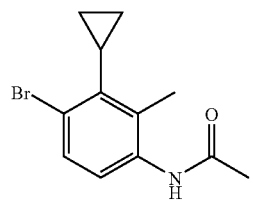

Under a nitrogen stream, to a solution of 185 g (0.978 mol) of 3-cyclopropyl-2-methylacetanilide (Reference compound 1) in 1800 ml of acetic acid, 88.2 g (1.08 mol) of sodium acetate was added. To the reaction solution, 55.1 ml (1.08 mol) of bromine was added dropwise at 20° C. to 30° C., and the resulting mixture was stirred at room temperature for 3 hours.

After the reaction was completed, to the reaction solution, 1800 ml of water and 300 ml of a 5% by weight aqueous solution of sodium bisulfite were added, and the resulting mixture was stirred at room temperature for 30 minutes. The resulting solid was collected by filtration, washed with 1000 ml of water and dried, whereby 242 g of the title compound was obtained as a white solid (yield: 92%).

Melting point: 170-172° C.
Rf value: 0.25 (n-hexane:ethyl acetate=1:1 (v/v))
Mass spectrum (CI, m/z): 268, 270 (M$^+$+1)
$^1$H-NMR spectrum (DMSO-d$_6$, δ ppm): 0.50-0.56 (m, 2H), 1.08-1.14 (m, 2H), 1.72-1.81 (m, 1H), 2.04 (s, 3H), 2.29 (s, 3H), 7.16 (d, J=8.5 Hz, 1H), 7.37 (d, J=8.5 Hz, 1H), 9.34 (brs, 1H)

Reference Example 3

Synthesis of 1-acetyl-5-bromo-4-cyclopropyl-1H-indazole (Reference Compound 3)

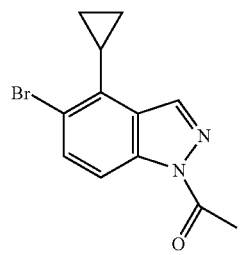

Under a nitrogen stream, to a solution of 228 g (0.850 mol) of 4-bromo-3-cyclopropyl-2-methylacetanilide (Reference compound 2) in 2280 ml of ethyl acetate, 13.7 g (0.042 mol) of tetra-n-butyl ammonium bromide, 167 g (1.70 mol) of potassium acetate, 240 ml (2.54 mol) of acetic anhydride, 230 ml (1.72 mol) of isoamyl nitrite were sequentially added, and the resulting mixture was stirred for 11 hours under a condition of heating to reflux.

After the reaction was completed, the reaction solution was cooled to room temperature, and 2280 ml of water was added to perform liquid separation. The deposited solid in the organic layer was collected by filtration and dried, whereby 139 g of the title compound was obtained as a pale yellow solid (yield: 59%).

Melting point: 125-126° C.
Rf value: 0.25 (n-hexane:ethyl acetate=9:1 (v/v))
Mass spectrum (CI, m/z): 279, 281 ($M^+$+1)
$^1$H-NMR spectrum (CDCl$_3$, ∈ ppm): 0.87-0.92 (m, 2H), 1.20-1.27 (m, 2H), 2.12-2.21 (m, 1H), 2.77 (s, 3H), 7.67 (d, J=8.8 Hz, 1H), 8.15-8.18 (m, 1H), 8.28 (d, J=0.7 Hz, 1H)

Reference Example 4

Synthesis of 5-bromo-4-cyclopropyl-1H-indazole (Reference Compound 4)

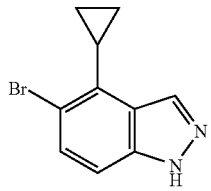

To a solution of 195 g (700 mmol) of 1-acetyl-5-bromo-4-cyclopropyl-1H-indazole (Reference compound 3) in 700 ml of a mixed solution of methanol:tetrahydrofuran (1:1 (v/v)), 120 ml (840 mmol) of a 7 N aqueous solution of sodium hydroxide was added at 10° C. to 20° C., and the resulting mixture was stirred at room temperature for 30 minutes.

After the reaction was completed, the reaction solution was neutralized with 2 N hydrochloric acid, 1400 ml of water was added thereto, and the resulting mixture was stirred at room temperature for 30 minutes. The resulting solid was collected by filtration, washed with 500 ml of water and dried, whereby 161 g of the title compound was obtained as a slightly orange solid (yield: 97%).

Melting point: 149-151° C.
Rf value: 0.65 (n-hexane:ethyl acetate=1:1 (v/v))
Mass spectrum (CI, m/z): 237, 239 ($M^+$+1)
$^1$H-NMR spectrum (DMSO-d$_6$, δ ppm): 0.96-1.01 (m, 2H), 1.12-1.19 (m, 2H), 2.19-2.28 (m, 1H), 7.31-7.34 (m, 1H), 7.46 (d, J=8.5 Hz, 1H), 8.11 (d, J=1.0 Hz, 1H), 13.23 (brs, 1H)

Reference Example 5

Synthesis of 5-bromo-4-cyclopropyl-1-(tetrahydro-pyran-2-yl)-1H-indazole (Reference Compound 5)

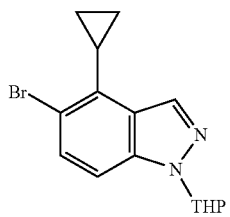

Under a nitrogen stream, to a solution of 154 g mol) of 5-bromo-4-cyclopropyl-1H-indazole (Reference compound 4) in 1040 ml of acetonitrile, 32.7 g mol) of pyridinium p-toluenesulfonate and 119 ml mol) of 3,4-dihydro-2H-pyran were added, and the resulting mixture was stirred at room temperature for 27 hours.

After the reaction was completed, to the reaction solution, 2300 ml of toluene was added, and the organic layer was sequentially washed with 1000 ml of a saturated aqueous solution of sodium hydrogen carbonate, 1000 ml of a saturated aqueous solution of ammonium chloride, 1000 ml of a saturated aqueous solution of sodium chloride, and 1000 ml of water, dried over anhydrous magnesium sulfate and concentrated under reduced pressure. To the resulting residue, 650 ml of methanol and 650 ml of water were added, and the resulting solid was collected by filtration, washed with water and dried, whereby 202 g of the title compound was obtained as an orange solid (yield: 97%).

Melting point: 75-76° C.
Rf value: 0.40 (n-hexane:ethyl acetate=4:1 (v/v))
Mass spectrum (EI, m/z): 320, 322 ($M^+$)
$^1$H-NMR spectrum (CDCl$_3$, δ ppm): 0.93-0.98 (m, 2H), 1.14-1.21 (m, 2H), 1.63-1.80 (m, 3H), 2.01-2.25 (m, 3H), 2.47-2.60 (m, 1H), 3.68-3.76 (m, 1H), 3.98-4.03 (m, 1H), 5.66 (dd, J1=9.4 Hz, J2=2.8 Hz, 1H), 7.28-7.32 (m, 1H), 7.50 (d, J=9.0 Hz, 1H), 8.12 (d, J=0.7 Hz, 1H)

Reference Example 6

Synthesis of 4-cyclopropyl-1-(tetrahydropyran-2-yl)-5-(4,4,5,5-tetramethyl[1,3,2]dioxaborolanyl)-1H-indazole (Reference Compound 6)

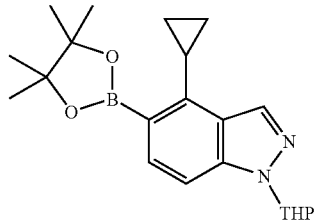

To a solution of 70 g (220 mmol) of 5-bromo-4-cyclopropyl-1-(tetrahydropyran-2-yl)-1H-indazole (Reference compound 5) in 490 ml of toluene, 91 ml (650 mmol) of triethylamine was added dropwise at room temperature under an argon stream with stirring. After the resulting mixture was subjected to bubbling with argon gas for 10 minutes, 4.6 g (6.6 mmol) of dichlorobis(triphenylphosphine) palladium, and then 63 ml (430 mmol) of 4,4,5,5-tetramethyl[1,3,2]dioxaborolane were added dropwise at room temperature under an argon stream with stirring, and the resulting mixture was stirred with heating at 110° C. for 6 hours.

After the reaction was completed, to the reaction solution, 14 ml of water, 350 ml of a 10% aqueous solution of citric acid and 14 g of Celite were added, and the resulting mixture was stirred for 10 minutes and then filtered. The filtrate was subjected to liquid separation, and to the organic layer, 350 ml of a saturated aqueous solution of sodium hydrogen carbonate and 14 g of Celite were added. The resulting mixture was stirred for 10 minutes and then filtered. The filtrate was subjected to liquid separation, and the organic layer was dried over anhydrous magnesium sulfate and concentrated under reduced pressure. To the resulting residue, 700 ml of n-heptane was added, and the resulting mixture was filtered through Celite, and the filtrate was concentrated under reduced pressure. The resulting residue was subjected to silica gel column chromatography (eluting solvent: n-hexane:ethyl acetate=9:1 (v/v)) and the fraction containing the desired substance was concentrated under reduced pressure, whereby 74 g of the title compound was obtained as a pale yellow oily substance (yield: 92%).

Rf value: 0.43 (n-hexane:ethyl acetate=4:1 (v/v))

Mass spectrum (CI, m/z): 369 (M$^+$+1)

$^1$H-NMR spectrum (CDCl$_3$, δ ppm): 0.93-1.15 (m, 4H), 1.37 (s, 12H), 1.55-1.87 (m, 3H), 1.97-2.25 (m, 2H), 2.45-2.65 (m, 1H), 2.65-2.80 (m, 1H), 3.65-3.80 (m, 1H), 3.95-4.10 (m, 1H), 5.65-5.75 (m, 1H), 7.34 (d, J=8.5 Hz, 1H), 7.71 (d, J=8.5 Hz, 1H), 8.11 (s, 1H)

Reference Example 7

Synthesis of 2-bromo-5-(5-cyano-spiro[2,3]hex-5-yl)pyridine (Reference Compound 7)

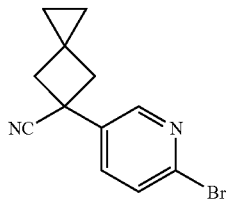

To a solution of 4.0 g (20 mmol) of 2-bromo-5-cyanomethylpyridine (see WO 2003/050087) in 40 ml of N,N-dimethylformamide, 2.0 g (46 mmol) of sodium hydride (55% sodium hydride dispersed in mineral oil) was added in divided portions at 0° C. under an argon stream with stirring. Then, a solution of 6.6 g (21 mmol) of 1,1-bis(iodomethyl)cyclopropane [see Michael E. Wright et al., J. Org. Chem., 58, 4122 (1993)] in 20 ml of N,N-dimethylformamide was added dropwise thereto at 0° C. with stirring, and the resulting mixture was stirred for 2 hours.

After the reaction was completed, the reaction solution was slowly poured into a saturated aqueous solution of ammonium chloride, and water was added thereto, and then, the mixture was extracted with toluene. The organic layer was washed with a saturated aqueous solution of sodium chloride, dried over anhydrous magnesium sulfate and concentrated under reduced pressure. The resulting residue was subjected to silica gel column chromatography (eluting solvent: n-hexane:ethyl acetate=4:1 (v/v)) and the fraction containing the desired substance was concentrated under reduced pressure, whereby 2.2 g of the title compound was obtained as a colorless oily substance (yield: 41%).

Rf value: 0.51 (n-hexane:ethyl acetate=4:1 (v/v))

Mass spectrum (CI, m/z): 263, 265 (M$^+$+1)

$^1$H-NMR spectrum (CDCl$_3$, δ ppm): 0.59-0.67 (m, 2H), 0.74-0.81 (m, 2H), 2.66-2.73 (m, 2H), 3.03-3.10 (m, 2H), 7.55 (dd, J1=8.4 Hz, J2=0.7 Hz, 1H), 7.73 (dd, J1=8.4 Hz, J2=2.7 Hz, 1H), 8.62 (dd, J1=2.7 Hz, J2=0.7 Hz, 1H)

Reference Example 8

Synthesis of 5-(5-aminocarbonyl-spiro[2,3]hex-5-yl)-2-bromopyridine (Reference Compound 8)

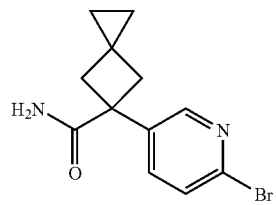

To a solution of 2.0 g (7.6 mmol) of 2-bromo-5-(5-cyano-spiro[2,3]hex-5-yl)pyridine (Reference compound 7) in 100 ml of n-heptane, 10 g of silica gel (PSQ 60B, manufactured by Fuji Silysia Chemical Ltd.) and 15 g of manganese dioxide were added and the resulting mixture was stirred at 90° C. for 2 hours.

After the reaction was completed, the reaction solution was cooled to room temperature and filtered through Celite. The resulting solid was washed 3 times with 300 ml of ethyl acetate, the filtrate and washing liquid were collected and the combined liquid was concentrated under reduced pressure. To the resulting residue, 10 ml of ethyl acetate and 50 ml of n-heptane were added, and the resulting mixture was subjected to an ultrasonic treatment. The resulting solid was collected by filtration and washed with n-heptane, whereby 1.6 g of the title compound was obtained as white powder (yield: 75%).

Melting point: 174-175° C.

Rf value: 0.19 (n-hexane:ethyl acetate=1:1 (v/v))

Mass spectrum (CI, m/z): 281, 283 (M$^+$+1)

$^1$H-NMR spectrum (CDCl$_3$, δ ppm): 0.40-0.65 (m, 4H), 2.55-2.65 (m, 2H), 2.90-3.00 (m, 2H), 5.35-5.80 (m, 2H), 7.49 (dd, J1=8.3 Hz, J2=1.0 Hz, 1H), 7.55 (dd, J1=8.3 Hz, J2=2.7 Hz, 1H), 8.40-8.45 (m, 1H)

Reference Example 9

Synthesis of 2-bromo-5-(5-tert-butoxycarbonylamino-spiro[2,3]hex-5-yl)pyridine (Reference Compound 9)

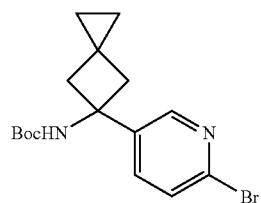

To a solution of 1.6 g (5.7 mmol) of 5-(5-aminocarbonyl-spiro[2,3]hex-5-yl)-2-bromopyridine (Reference compound 8) in 16 ml of tert-butanol, 2.7 g (6.3 mmol) of [bis(trifluoroacetoxy)iodo]benzene was added at room temperature under an argon stream with stirring, and the resulting mixture was stirred with heating at 60° C. for 20 minutes. Then, 1.0 ml (12 mmol) of pyridine was added thereto, and the resulting mixture was stirred with heating at 90° C. for 30 minutes.

After the reaction was completed, the reaction solution was concentrated under reduced pressure. To the resulting residue, 100 ml of toluene was added, and the organic layer was washed 3 times with 50 ml of water, and then washed with 50 ml of a saturated aqueous solution of sodium hydrogen carbonate. The washed organic layer was dried over anhydrous magnesium sulfate and concentrated under reduced pressure. The resulting residue was subjected to silica gel column chromatography (eluting solvent: n-hexane:ethyl acetate=4:1 (v/v)) and the fraction containing the desired substance was concentrated under reduced pressure. To the resulting residue, n-heptane was added and the resulting solid was collected by filtration and washed with n-haptane, whereby 1.0 g of the title compound was obtained as white powder (yield: 50%).

Melting point: 122-123° C.
Rf value: 0.40 (n-hexane:ethyl acetate=4:1 (v/v))
Mass spectrum (CI, m/z): 353, 355 ($M^+$+1)
$^1$H-NMR spectrum (CDCl$_3$, δ ppm): 0.50-0.70 (m, 4H), 1.40 (brs, 9H), 2.45-2.75 (m, 4H), 5.26 (brs, 1H), 7.45 (dd, J1=8.3 Hz, J2=0.5 Hz, 1H), 7.65-7.80 (m, 1H), 8.46-8.60 (m, 1H)

Example 1

Synthesis of 5-{5-(5-tert-butoxycarbonylamino-spiro [2,3]hex-5-yl)pyridin-2-yl)}-4-cyclopropyl-1-(tetrahydropyran-2-yl)-1H-indazole (Example Compound 1)

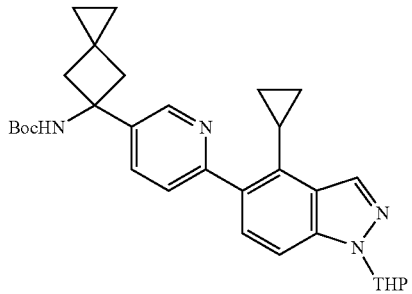

To a solution of 1.0 g (2.7 mmol) of 4-cyclopropyl-1-(tetrahydropyran-2-yl)-5-(4,4,5,5-tetramethyl[1,3,2]dioxaborolanyl)-1H-indazole (Reference compound 6) in 6 ml of toluene, 1.2 ml of ethanol, 1.2 ml of water, 2.1 g (8.5 mmol) of potassium phosphate dihydrate, and 1.0 g (2.8 mmol) of 2-bromo-5-(5-tert-butoxycarbonylamino-spiro[2,3]hex-5-yl)pyridine (Reference compound 9) were added under an argon stream, and the resulting mixture was subjected to bubbling with argon gas for 10 minutes. Then, 0.090 ml (0.057 mmol) of a 20% by weight solution of tricyclohexylphosphine in toluene and 6.4 mg (0.029 mmol) of palladium acetate were added thereto under an argon stream, and the resulting mixture was stirred with heating at 90° C. for 5 hours.

After the reaction was completed, to the reaction solution, 10 ml of toluene and 5 ml of water were added, and the resulting mixture was subjected to liquid separation. The organic layer was dried over anhydrous magnesium sulfate and concentrated under reduced pressure. The resulting residue was subjected to silica gel column chromatography (eluting solvent: n-hexane:ethyl acetate=2:1 (v/v)) and the fraction containing the desired substance was concentrated under reduced pressure. To the resulting residue, 10 ml of ethyl acetate and 20 ml of n-heptane were added and the resulting solid was collected by filtration, whereby 700 mg of the title compound was obtained as white powder (yield: 48%).

Melting point: 199-202° C.
Rf value: 0.33 (n-hexane:ethyl acetate=1:1 (v/v))
Mass spectrum (CI, m/z): 515 ($M^+$+1)
$^1$H-NMR spectrum (CDCl$_3$, δ ppm): 0.45-0.70 (m, 6H), 0.80-0.95 (m, 2H), 1.41 (brs, 9H), 1.60-1.90 (m, 3H), 2.00-2.24 (m, 2H), 2.27-2.40 (m, 1H), 2.50-2.80 (m, 5H), 3.70-3.82 (m, 1H), 4.00-4.10 (m, 1H), 5.28 (brs, 1H), 5.70-5.78 (m, 1H), 7.49 (d, J=8.6 Hz, 1H), 7.52-7.63 (m, 2H), 7.80-7.95 (m, 1H), 8.22 (s, 1H), 8.85-8.95 (m, 1H)

Example 2

Synthesis of 5-{5-(5-amino-spiro[2,3]hex-5-yl)pyridin-2-yl)}-4-cyclopropyl-1H-indazole Dihydrochloride (Example Compound 2)

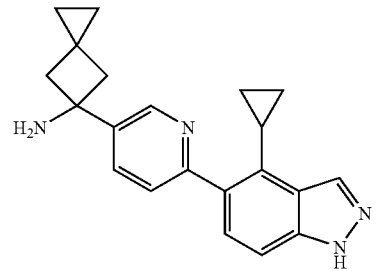

To 700 mg (1.4 mmol) of 5-{5-(5-tert-butoxycarbonyl amino-spiro[2,3]hex-5-yl)pyridin-2-yl)}-4-cyclopropyl-1-(tetrahydropyran-2-yl)-1H-indazole (Example compound 1), 2 ml of ethanol, 0.1 ml of water and 5 ml of a 36% by weight solution of hydrogen chloride in ethanol were added, and the resulting mixture was stirred at room temperature for 3 hours and then at 35° C. for 2 hours under an argon stream.

After the reaction was completed, the reaction solution was cooled to room temperature, and 1 ml of ethanol was added thereto. The resulting mixture was filtered, and the residue was washed with ethanol. To the resulting solid, 1.5 ml of ethanol and 0.3 ml of water were added at 80° C. and the resulting mixture was stirred with heating for 15 minutes thereby dissolving the solid.

The resulting solution was cooled to 0° C., and 1.5 ml of ethanol was added thereto. The resulting solid was collected by filtration and washed with ethanol, whereby 300 mg of the title compound was obtained as white powder (yield: 55%).

Melting point: >300° C. (decomposition)
Rf value: 0.30 (chloroform:methanol: 28% ammonia water=5:1:0.01 (v/v/v))
Mass spectrum (CI, m/z): 331 ($M^+$+1)
$^1$H-NMR spectrum (DMSO-d$_6$, δ ppm): 0.40-0.73 (m, 6H), 0.80-1.00 (m, 2H), 2.44-2.54 (m, 1H), 2.74 (d, J=13.9 Hz, 2H), 2.97 (d, J=13.9 Hz, 2H), 7.45-7.65 (m, 2H), 8.07 (d, J=8.3 Hz, 1H), 8.27 (s, 1H), 8.5 (d, J=8.3 Hz, 1H), 9.00-9.08 (m, 1H), 9.10-9.40 (m, 3H), 13.2 (brs, 1H)

Preparation Examples

Hereinafter, general preparation examples of the present invention compound will be shown.

1) Tablet
Formulation 1 (in 100 mg)

| | |
|---|---|
| Present invention compound | 1 mg |
| Lactose | 66.4 mg |
| Corn starch | 20 mg |
| Carboxymethyl cellulose calcium | 6 mg |
| Hydroxypropyl cellulose | 4 mg |
| Magnesium stearate | 0.6 mg |

The tablet having the above formulation is coated with 2 mg of a coating agent (a common coating agent such as hydroxypropylmethyl cellulose, macrogol or a silicone resin), whereby a desired coated tablet is obtained (the same shall apply to a tablet having the following formulation). Further, a desired tablet can be obtained by appropriately changing the kind and amount of the present invention compound and additives.

2) Capsule
Formulation 2 (in 150 mg)

| | |
|---|---|
| Present invention compound | 5 mg |
| Lactose | 145 mg |

A desired capsule can be obtained by appropriately changing the mixing ratio of the present invention compound to lactose.

3) Eye drop
Formulation 3 (in 100 ml)

| | |
|---|---|
| Present invention compound | 100 mg |
| Sodium chloride | 900 mg |
| Polysorbate 80 | 200 mg |
| Sodium hydroxide | q.s. |
| Hydrochloric acid | q.s. |
| Sterile purified water | q.s. |

A desired eye drop can be obtained by appropriately changing the kind and amount of the present invention compound and additives.

Pharmacological Test

A. Test for Evaluation of Rho Kinase Inhibitory Activity

In order to study the usefulness of the present invention compound as a Rho kinase inhibitor, in accordance with the method described in J. Biol. Chem., 274, 32418 (1999) and the method described in the instruction manual for use attached to the commercially available activated ROCK-II [Upstate Biotechnology, Catalog No. 14-338 (5 units/50 µl)], the Rho kinase inhibitory activity of the present invention compound was evaluated and studied. As a test compound, Example compound 2 was used.

Preparation of Reagents

1) Preparation of Buffer

A buffer containing 50 mM trishydroxymethylaminomethane (Tris) (pH 7.5), 2 mM ethyleneglycol-bis(β-aminoethyl ether)-N,N,N',N'-tetraacetic acid (EGTA), 1 mM ethylenediaminetetraacetic acid (EDTA), 5 mM magnesium chloride ($MgCl_2$), 5 mM β-glycerol phosphate and 2 mM dithiothreitol (DTT) was prepared by adding these ingredients to distilled water.

2) Preparation of [γ-$^{32}$P]ATP Solution

A mixed liquid of a 10 mM aqueous solution of ATP and a commercially available [γ-$^{32}$P]ATP solution [NEN, Code No. NEG-002A] was diluted with the buffer, whereby a 300 µM [γ-$^{32}$P]ATP solution was prepared.

3) Preparation of ROCK-II Solution

A commercially available activated ROCK-II [Upstate Biotechnology, Catalog No. 14-338, (5 units/50 µl)] was diluted to 1/100 with the buffer, whereby a ROCK-II solution was prepared.

4) Preparation of 1 mM Substrate Solution

S6 kinase substrate peptide (Upstate Biotechnology, Catalog No. 12-124) (2 mg) was dissolved in distilled water, whereby a 1 mM substrate solution was prepared.

5) Preparation of Phosphoric Acid Solutions

Commercially available phosphoric acid was diluted with distilled water, whereby phosphoric acid solutions with various concentrations were prepared.

6) Preparation of Test Compound Solution

The test compound was dissolved in a 10% aqueous solution of dimethyl sulfoxide (DMSO).

Evaluation Method

1) After 5 µl of the test compound solution and 5 µl of the [γ-$^{32}$P]ATP solution are placed in a microtube, the resulting mixture was cooled to 4° C.

2) Then, 10 µl of the ROCK-II solution, 2.5 µl of the 1 mM substrate solution and 37.5 µl of the buffer are added thereto, whereby a reaction mixture is prepared. The reaction mixture is cooled to 4° C.

3) The microtube is incubated in a water bath (30° C.) for 15 minutes.

4) After the microtube is cooled to 4° C., 5 µl of a 250 mM phosphoric acid solution is added to the microtube to stop the reaction.

5) 30 µl of the reaction mixture is spotted on a filter paper (Whatman P81) (trade name).

6) In order to wash out unreacted [γ-$^{32}$P]ATP, the filter paper is transferred to a beaker containing a 75 mM phosphoric acid solution and the beaker is shaken for 5 minutes. The filter paper is washed four more times using this phosphoric acid solution.

7) The filter paper is dipped in ethanol and then dried. Thereafter, the amount of phosphorylated substrate is measured using a liquid scintillation counter.

Calculation of $IC_{50}$

A difference between the amount of phosphorylated substrate in a background microtube in which the buffer is placed instead of the ROCK-II solution and the amount of phosphorylated substrate in a control microtube in which a 10% aqueous solution of DMSO is placed instead of the test compound solution is assumed to be 100%. The amount of phosphorylated substrate in the microtube in which the test compound solution is placed is interpolated, and the amount of phosphorylated substrate at the time of adding the test compound solution is calculated as a relative value. Based on the amounts of phosphorylated substrate at the time of adding the test compound solutions of various concentrations, the concentration of the test compound solution at which the enzyme activity is inhibited by 50% is calculated as $IC_{50}$.

Calculation of Ki Value

The Ki value is calculated according to the following calculation formula. S represents the concentration of ATP contained in the reaction mixture, and Km represents the Michaelis-Menten constant.

$$Ki=IC_{50}/(1+S/Km)$$

Result and Discussion

The result when Example compound 2 was used as the test compound is shown in Table 1.

TABLE 1

| Test compound | Ki value (nM) |
|---|---|
| Example compound 2 | 3.5 |

As shown in Table 1, the test compound exhibited an excellent Rho kinase inhibitory activity. From this result, it was found that the present invention compound is very useful as a therapeutic agent for diseases associated with Rho kinase.

B. Test for Measurement of Intraocular Pressure-Reducing Activity

In order to study the usefulness of the present invention compound as a therapeutic agent for glaucoma, an intraocular pressure-reducing effect in the case where the present invention compound was administered to cynomolgus monkeys (sex: male; one group consisting of 4 to 5 monkeys) was evaluated and studied. As a test compound, Example compound 2 (hereinafter referred to as the test compound) was used.

Preparation of Test Compound Solution

The test compound was dissolved in a 2.6% glycerin solution, and sodium hydroxide was added thereto to adjust the pH (pH 6.0 to 7.0), whereby a 0.1% test compound solution was prepared.

Test Method for Evaluation of Reduction of Intraocular Pressure

1) One drop of a 0.4% oxybuprocaine hydrochloride eye drop was instilled into both eyes of the cynomolgus monkeys to achieve local anesthesia.

2) The intraocular pressure was measured immediately before administration of the test compound solution, which was defined as the initial intraocular pressure.

3) The test compound solution was instilled into one of the eyes of the experimental animals (the other eye was not treated).

4) At 2, 4 and 6 hours after instillation of the test compound solution, one drop of a 0.4% oxybuprocaine hydrochloride eye drop was instilled into both eyes to achieve local anesthesia and then the intraocular pressure was measured. Measurement of the intraocular pressure for each time was carried out three times and a mean value thereof was calculated.

In a control group, the test was performed by the same procedure as described in the above 1) to 4) except that only a vehicle (a 2.6% glycerin solution) was administered in place of the test compound solution.

Result and Discussion

The result when the test compound was used is shown in FIG. 1. Further, the intraocular pressure is represented by a value of a change from the initial intraocular pressure.

As shown in FIG. 1, the test compound exhibited an excellent intraocular pressure-reducing activity. From this result, it was found that the present invention compound is particularly useful as a therapeutic agent for glaucoma.

INDUSTRIAL APPLICABILITY

The indazole derivative according to the present invention has a Rho kinase inhibitory activity and is useful as a therapeutic agent for diseases associated with Rho kinase such as eye diseases including glaucoma.

BRIEF DESCRIPTION OF THE DRAWINGS

FIG. 1 is a graph showing a change in the intraocular pressure over time in each administration group. The intraocular pressure is represented by a value of a change from the initial intraocular pressure. □ represents a test compound administration group; and ○ represents a control group.

The invention claimed is:

1. A compound represented by the following formula [I] or a salt thereof:

[I]

wherein the ring X represents a benzene ring or a pyridine ring;

$R^1$ and $R^2$ are the same or different and represent one or plural groups selected from the group consisting of a hydrogen atom, a substituted or unsubstituted alkyl group and a substituted or unsubstituted cycloalkyl group;

$R^3$ represents one or plural groups selected from the group consisting of a hydrogen atom and a substituted or unsubstituted alkyl group;

$R^4$ and $R^5$ are the same or different and represent one or plural groups selected from the group consisting of a hydrogen atom and a substituted or unsubstituted alkyl group;

$R^6$ and $R^7$ are the same or different and represent a group selected from the group consisting of a hydrogen atom and a substituted or unsubstituted alkyl group;

$R^6$ and $R^7$ may be joined together to form a monocyclic heterocyclic ring; and m, n, p and q are the same or different and represent an integer of 0 to 3, with the proviso that the sum of m and n is an integer of 1 or more and the sum of p and q is an integer of 1 or more, wherein the substituted alkyl group is substituted with one or plural groups selected from the group consisting of a halogen atom, a hydroxyl group, an unsubstituted alkoxy group, an unsubstituted aryl group, a hydroxyimino group and an unsubstituted alkoxyimino group.

2. The compound or a salt thereof according to claim 1, wherein in the formula [I], the ring X represents a benzene ring or a pyridine ring;

$R^1$ represents a hydrogen atom or a substituted alkyl group;

$R^2$ represents a hydrogen atom, a substituted or unsubstituted alkyl group or an unsubstituted cycloalkyl group;

$R^3$ represents a hydrogen atom;

$R^4$ and $R^5$ represent a hydrogen atom;

$R^6$ and $R^7$ represent a hydrogen atom; and m, n, p and q are the same or different and represent an integer of 0 to 2, with the proviso that the sum of m and n is an integer of 1 or more and the sum of p and q is an integer of 1 or more.

3. The compound or a salt thereof according to claim 2, wherein the substituted alkyl group represents an alkyl group substituted with one or plural groups selected from the group consisting of a hydroxy group and a hydroxyimino group.

4. The compound or a salt thereof according to claim 1, wherein in the formula [I], the ring X represents a benzene ring or a pyridine ring;

$R^1$ represents a hydrogen atom, a hydroxymethyl group or a hydroxyiminomethyl group;

$R^2$ represents a hydrogen atom, an ethyl group, a hydroxymethyl group, a 1-hydroxyethyl group, a 2-hydroxyethyl group, a cyclopropyl group, a cyclobutyl group, a cyclopentyl group or a cyclohexyl group;

$R^3$ represents a hydrogen atom;

$R^4$ and $R^5$ represent a hydrogen atom;

$R^6$ and $R^7$ represent a hydrogen atom;

m and n represent 1; and one of p and q represents 0 and the other represents 1.

5. The compound or a salt thereof according to claim 1, wherein in the formula [I], the ring X is substituted at the 5-position of the indazole ring.

6. A compound selected from the group consisting of:
- 5-{5-(1-amino-spiro[2,2]pent-1-yl)pyridin-2-yl}-4-cyclopropyl-1H-indazole,
- 5-{5-(1-amino-spiro[2,3]hex-1-yl)pyridin-2-yl}-4-cyclopropyl-1H-indazole,
- 5-{5-(5-amino-spiro[2,3]hex-5-yl)pyridin-2-yl}-4-cyclopropyl-1H-indazole,
- 5-{4-(5-amino-spiro[2,3]hex-5-yl)phenyl}-4-cyclopropyl-1H-indazole, and
- 5-{5-(2-amino-spiro[3,3]hept-2-yl)pyridin-2-yl}-4-cyclopropyl-1H-indazole, or a salt thereof.

7. A pharmaceutical composition comprising the compound or a salt thereof according to claim 1 or 6 and a pharmaceutically acceptable carrier.

8. A method of inhibiting Rho kinase comprising administering an effective amount of the compound or a salt thereof according to claim 1 or 6 to a patient.

9. A method of treating glaucoma comprising administering an effective amount of the compound or a salt thereof according to claim 1 or 6 to a patient.

* * * * *